(12) United States Patent
Cooper et al.

(10) Patent No.: US 7,539,282 B2
(45) Date of Patent: May 26, 2009

(54) XRF ANALYZER

(75) Inventors: John Arthur Cooper, Beaverton, OR (US); Sarah Catherine Fry, Beaverton, OR (US); Bruce Edward Johnsen, Tigard, OR (US)

(73) Assignee: Cooper Environmental Services LLC, Portland, OR (US)

( * ) Notice: Subject to any disclaimer, the term of this patent is extended or adjusted under 35 U.S.C. 154(b) by 966 days.

(21) Appl. No.: 11/101,792

(22) Filed: Apr. 7, 2005

(65) Prior Publication Data

US 2008/0310588 A1   Dec. 18, 2008

(51) Int. Cl.
*G01N 23/223*   (2006.01)

(52) U.S. Cl. .............................. 378/47; 378/44; 378/45; 378/48

(58) Field of Classification Search .................. 378/44, 378/45, 47, 48
See application file for complete search history.

(56) References Cited

U.S. PATENT DOCUMENTS

| | | | | |
|---|---|---|---|---|
| H188 H | * | 1/1987 | Thomson et al. | ............... 378/45 |
| 5,544,218 A | * | 8/1996 | Turner et al. | ................. 378/208 |
| 5,841,016 A | * | 11/1998 | Hossain et al. | ................ 73/1.01 |
| 6,012,325 A | * | 1/2000 | Ma | ............................ 73/24.02 |
| 6,735,276 B2 | * | 5/2004 | Ikeshita et al. | ................. 378/45 |
| 7,016,463 B2 | * | 3/2006 | Moriyama et al. | ............. 378/47 |
| 7,200,200 B2 | * | 4/2007 | Laurila et al. | ................... 378/45 |
| 7,254,212 B2 | * | 8/2007 | Saitoh et al. | ................... 378/47 |
| 7,277,527 B2 | * | 10/2007 | Gallagher | .................... 378/141 |

* cited by examiner

*Primary Examiner*—Allen C. Ho
(74) *Attorney, Agent, or Firm*—Jared S. Goff; Goff Patent Law, PLLC

(57) ABSTRACT

A method of analyzing a fluid sample by XRF includes the steps of: depositing the fluid sample onto a substrate, exposing the sample and the substrate to an x-ray emission, generating a first analytical signal responsive to the x-ray emission, providing an operable first reference material having a first extended position above the substrate and in communication with the x-ray emission, periodically extending the first reference material to its first extended position, generating a first calibration signal, providing an operable second reference material having a first extended position below the substrate and in communication with the x-ray emission, and periodically extending the second reference material to its first extended position and generating at least one second calibration signal. The first and second calibration signals are compared with predetermined values. The first and second reference materials also have second retracted positions.

8 Claims, 4 Drawing Sheets

XRF ANALYZER

BACKGROUND OF THE INVENTION

1. Technical Field

This invention relates to an x-ray fluorescence (XRF) analyzer and calibration methods of the x-ray fluorescence analyzer.

2. Field of the Invention

XRF is widely used to analyze a sample mass collected on a filter. An XRF analysis system includes three major components: an x-ray source, a sample and an x-ray detector. High energy x-rays are emitted from the x-ray source onto the sample to be analyzed. When the high energy x-rays hit the sample, new x-rays of differing energies are produced that are detected by the detector. The new x-ray energies are unique for each element in the sample. This process provides a spectrum, or chemical fingerprint, of the sample. The spectrum for each sample is analyzed to determine the components of the sample and the concentrations of those components.

XRF is a non-destructive analysis technique. Therefore, a sample analyzed by XRF is still available for reanalysis by XRF or another method. The technique can measure small concentrations in a relatively short analysis time for a wide range of elements. The accuracy of the XRF technique is limited to a specific dynamic range between the detection limits on the low end and saturation of the sample filter by particulate matter on the high end.

These sample measurements can provide plant operators with valuable information on plant efficiency, compliance efforts, and relationships between feedstock and emissions. On the other hand, inaccurate measurements could result in unnecessary regulatory restrictions, damage to health and the environment, and inappropriate plant operations.

In certain instances, it would be advantageous to use XRF to monitor the emissions of certain elements and compounds. The ability to use a continuous monitoring device based on X-ray fluorescence over long periods of time with confidence depends on the instrument's ability to provide automated quality assurance (QA) data proving that the instrument is working properly and that the results can be relied on at least to the accuracy and precision justified by the QA data. This is particularly important for continuous metals monitors that use filter tape to separate aerosol species from a gas stream and analyze the resulting deposits for metal content with X-ray fluorescence methods.

A problem with the prior art is that frequent calibration and quality assurance testing of the XRF analyzer is necessary if one wishes to rely on the results for proof of compliance with regulatory standards. Manual calibration and quality assurance take a lot of time and require the machine to be off-line.

BRIEF SUMMARY OF THE INVENTION

One object of the XRF analyzer is to incorporate new, innovative approaches to solve the problem of providing automated QA data.

A further object of the present invention is to provide procedures and mechanisms to confirm and document the accuracy and precision of the instrument's results.

Another object of the XRF analyzer according to the present invention is to provide a means to automatically test for and record QA test results.

A further object of the XRF analyzer according to the present invention is to automatically perform an energy calibration.

Another object of the present invention is to provide a procedure by which an energy calibration is automatically checked and adjusted if necessary.

To accomplish the above-state objectives, an XRF analyzer is provided wherein the XRF analyzer comprises an x-ray source, a filter tape, an x-ray detector, and calibration rods of known composition above and/or below the filter tape. The x-ray source hits one or both of the calibration rods and the reflected x-rays are detected by the x-ray detector. The reflected x-rays are analyzed to obtain desired calibration or QA data.

BRIEF DESCRIPTION OF THE DRAWINGS

The nature, principle and utility of the present invention will be clearly understood from the following detailed description when read in conjunction with the accompanying drawings, wherein.

The drawings are for illustrative purposes only and are not drawn to scale. In the drawings, the same numbers are used for the same part or portion throughout the drawings.

DETAILED DESCRIPTION OF THE INVENTION

Figure 1:
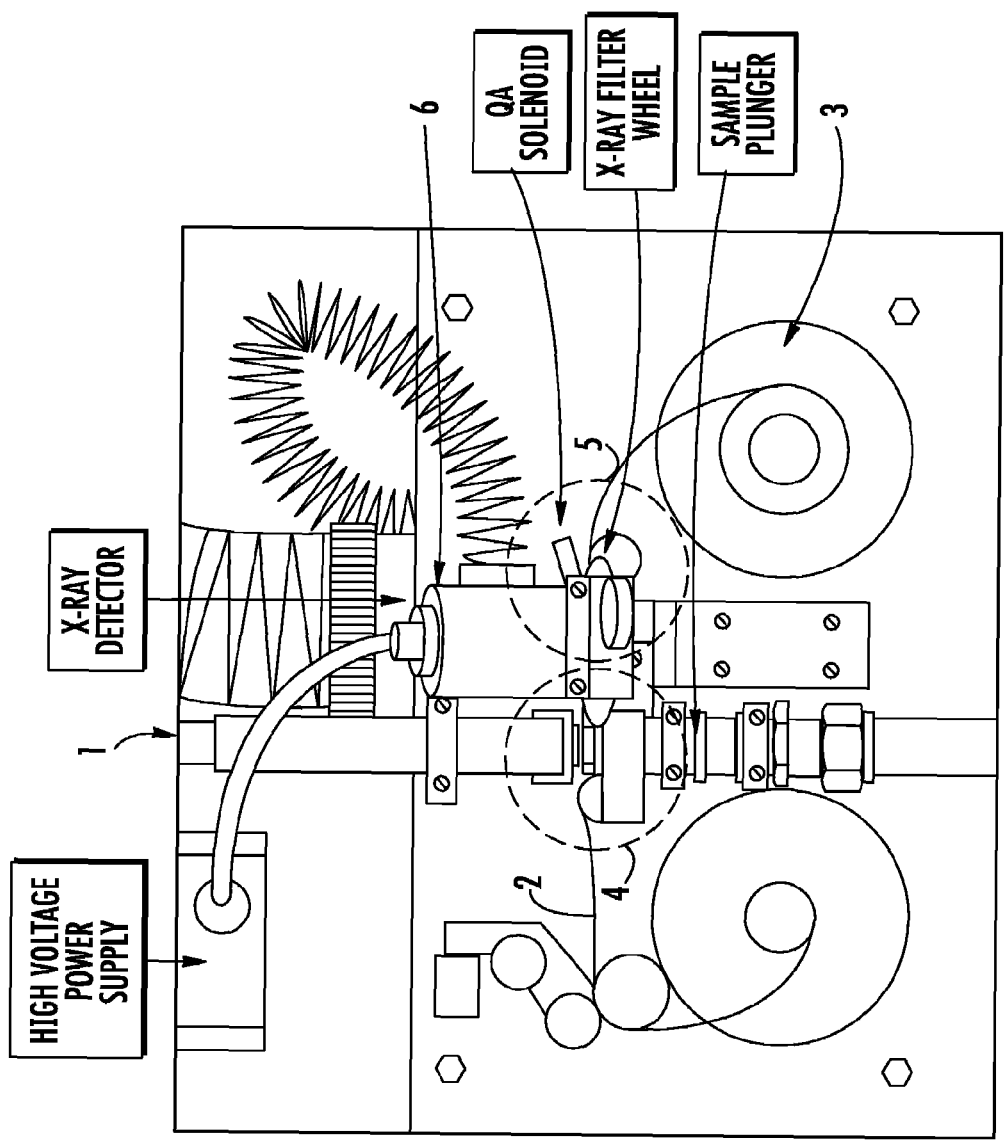
FIG. 1 is a schematic illustration of the XRF analyzer.

In the XRF analyzer shown in FIG. 1, a sample of stack gas is passed through the inlet tube 1 and deposited on a chemically treated filter 2 in the sample zone 4. The filter tape wheels 3 advance the filter tape to the analysis zone 5 where it is exposed to x-rays from the x-ray source 6.

Figure 2:
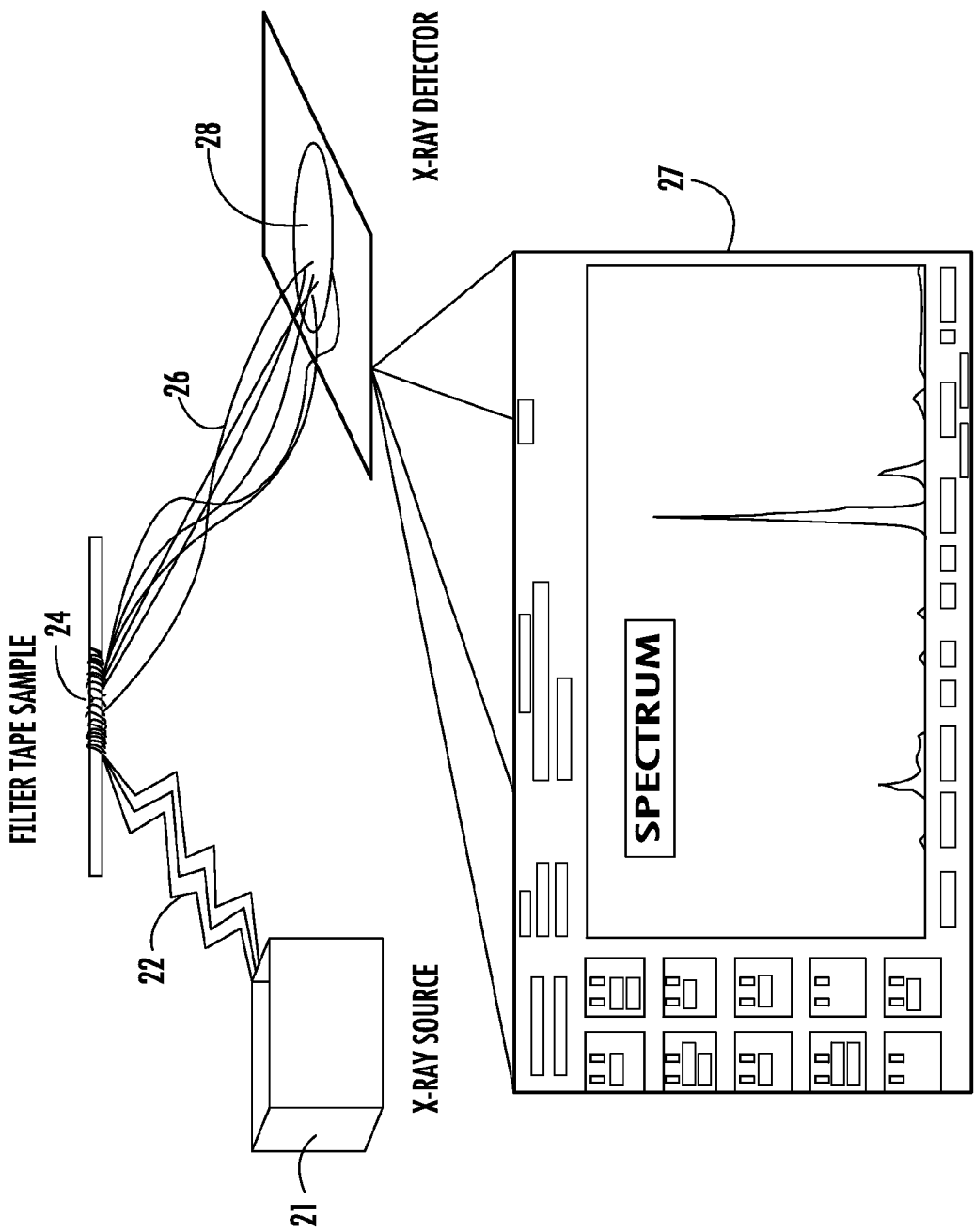
FIG. 2 is an illustration of the XRF technique.

As shown in more detail in FIG. 2, when the x-rays 22 from the x-ray source 21 hit the sample 24, new x-rays 26 of differing energies are produced and detected by the x-ray detector 28. The unique response of each sample component to the x-rays provides a spectrum 27 of each component contained in the sample. The spectrum 27 is used to determine the presence and concentrations of each component of the sample.

Figure 3:
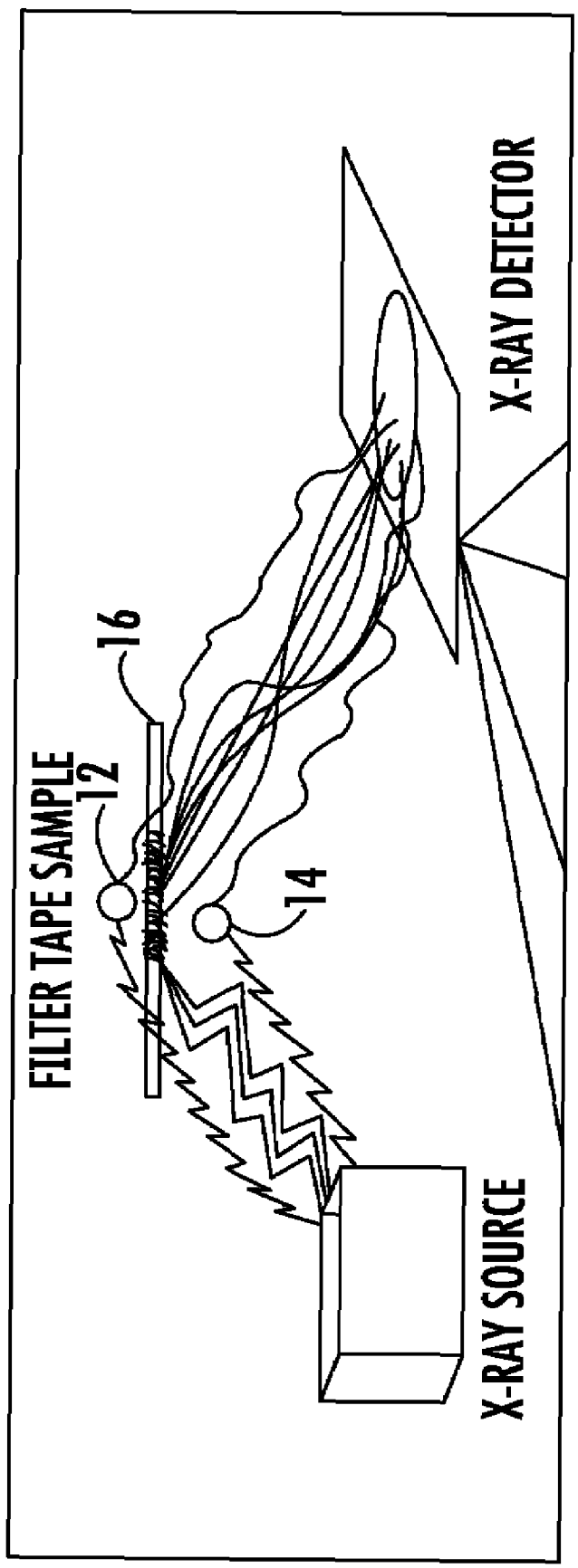
FIG. 3 is an illustration of an XRF calibration or QA technique according to a first embodiment.
Figure 4:
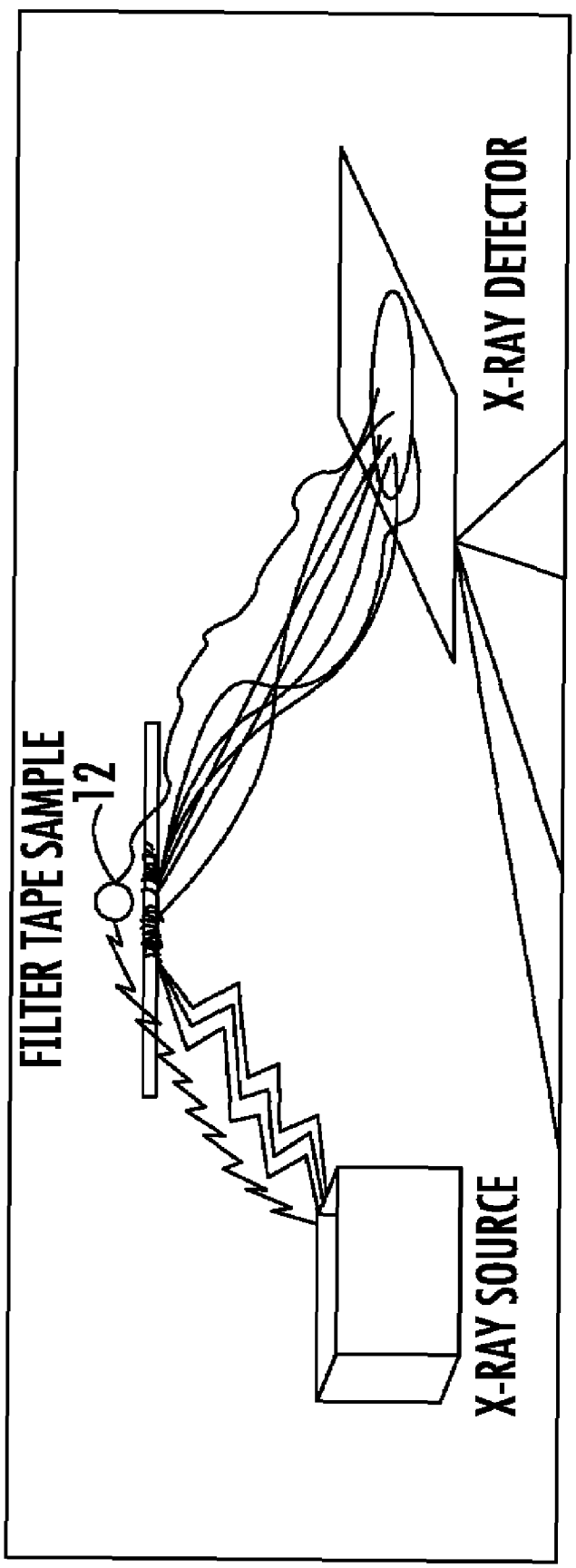
FIG. 4 is an illustration of an XRF calibration or QA technique according to a second embodiment.

To perform calibration or quality assurance tests, calibration rods 12 and 14 are inserted above and below the filter tape 16 as shown in FIG. 3. X-rays may pass through the filter tape 16 and hit rod 12. In addition, the x-rays may hit rod 14 before getting to the filter tape 16. The calibration rods 12 and 14 have an extended position, as shown in FIG. 3, wherein the rods 12 and 14 are inserted in the analysis zone. Alternatively, rods 12 and 14 have a retracted position wherein the rod is removed from the analysis zone. FIG. 4 shows rod 12 in the extended position while rod 14 is in the retracted position and is therefore not shown. Alternatively, rod 14 could be in the extended position while rod 12 is in the retracted position, or both rods could be in the retracted position (as shown in FIG. 2).

Calibration rods 12 and 14 are preferably operated by a plunger. The extended position of the rods 12 and 14 is reproducible, meaning that the rods are inserted in the same position each time they are extended.

Each rod may be made of a pure element, such as copper, or may be made of multiple metals. In the multi-metal rod, analyte metals of interest are incorporated into a resin which is then attached to the end of a rod.

EXAMPLES

Quality assurance evaluation test #1 is a quantitative calibration check. It consists of presenting one or more analytes at concentrations near the upper range to the instrument and comparing the reported concentration to the concentration reported when the instrument was last calibrated for concentrations (concentration versus intensity). In this test, a multi-metal rod is periodically inserted into the analysis zone (either above or below the filter) and the reported instrumental concentration is compared to the concentration reported the last time the instrument was calibrated for concentration.

Quality assurance evaluation test #2 is a zero or blank check. This is a check of the zero or response to a blank portion of the filter tape. It consists of automatically advancing the tape to a portion of the tape where there is no sample deposit. This portion of the tape therefore represents a blank or zero concentration. This unexposed portion of the tape is then analyzed automatically and the resulting concentration statistically compared to the "zero" concentration reported at the time of the last concentration calibration.

Quality assurance evaluation test #3 is an instrument stability check. Whereas the quantitative calibration check and the zero or blank check are performed periodically (once per day, for example), this test is performed with each deposit sample analyzed. It consists of monitoring the X-ray intensity of a non-analyte, non-interfering element placed in the analysis zone. It may be rigidly fixed in place or inserted and can be either above or below the filter. By monitoring, recording and comparing an X-ray peak intensity for this stability check element, the data user is assured that the X-ray analysis conditions periodically measured with other quality assurance and energy calibration tests were applicable with each and every sample analyzed.

Automated energy calibration test #1 consists of inserting a known element in any particular convenient form into the instrument's analysis zone, which may be either above or below the filter tape. The instrumental response to this element is compared to the known energy of an X-ray in the energy-intensity spectrum. The instrument's amplifier gain and/or zero are adjusted until the difference between the known energy and the instrument energy are minimized. This check can be done at intervals convenient for the particular application.

While the invention has been described by reference to the preferred embodiments described above those skilled in the art will recognize that the invention as described and illustrated can be modified in arrangement and detail without departing from the scope of the invention.

What is claimed is:

1. A method of analyzing a fluid sample by x-ray fluorescence comprising the steps of:
    providing a fluid sample;
    depositing a first portion of the fluid sample onto a substrate;
    exposing the first portion and the substrate to an x-ray emission;
    detecting x-rays produced by the x-ray emission hitting the first portion and the substrate;
    generating a first analytical signal responsive to the detected x-rays;
    providing an operable first reference material having a first extended position above the substrate and in communication with the x-ray emission, and a second retracted position;
    periodically extending the first reference material to its first extended position;
    generating a first calibration signal;
    providing an operable second reference material having a first extended position below the substrate and in communication with the x-ray emission and a second retracted position; and
    periodically extending the second reference material to its first extended position and generating at least one second calibration signal.

2. A method according to claim 1 further comprising comparing the first calibration signal with a predetermined value.

3. A method according to claim 1 further comprising comparing the second calibration signal with a predetermined value.

4. A method according to claim 1 further comprising comparing the first and second calibration signals with predetermined values.

5. A method according to claim 1 further comprising, before the step of periodically extending the second reference material to its first extended position and generating at least one second calibration signal, the step of positioning a clean substrate portion in communication with the x-ray emission.

6. A method according to claim 1 wherein the first calibration signal comprises a sensitivity measurement.

7. A method according to claim 1, wherein the second calibration signal comprises a precision measurement.

8. A method according to claim 1, wherein the steps of generating the first calibration signal and generating the second calibration signal are performed simultaneously.

* * * * *